United States Patent [19]

Muchowski et al.

[11] 4,296,042

[45] Oct. 20, 1981

[54] PREPARATION OF UNSATURATED ALIPHATIC INSECT PHEROMONES USING CYCLIC PHOSPHONIUM YLIDS

[75] Inventors: Joseph M. Muchowski, Sunnyvale; Michael C. Venuti, San Francisco, both of Calif.

[73] Assignee: Syntex (U.S.A.) Inc., Palo Alto, Calif.

[21] Appl. No.: 160,711

[22] Filed: Jun. 18, 1980

[51] Int. Cl.$^3$ .................. C07D 309/06; C07C 41/18; C07F 7/04

[52] U.S. Cl. .................. 260/345.9 R; 260/395; 542/412; 556/405; 556/482; 556/436; 560/234; 560/240; 568/12; 568/15; 568/626; 568/442

[58] Field of Search .................. 260/345.9 R, 395; 560/240, 234; 568/626, 12, 15; 556/482, 405; 542/412

[56] References Cited

U.S. PATENT DOCUMENTS

| | | | |
|---|---|---|---|
| 3,671,558 | 6/1972 | Siddal et al. | 260/410.9 R |
| 3,712,880 | 1/1973 | Siddall | 560/240 |
| 3,732,282 | 5/1973 | Henrick et al. | 260/465.9 |
| 3,919,329 | 11/1975 | Anderson et al. | 560/240 |
| 3,989,729 | 11/1976 | Anderson et al. | 560/208 |
| 3,996,270 | 12/1976 | Friedman et al. | 260/345.9 R |

OTHER PUBLICATIONS

Henrick, Tetrahedron, vol. 33, pp. 1845-1889 (1977).
Johnson, "Ylid Chemistry", Academic Press, Inc., New York (1966) pp. 23-32, 125-131.
Sonnet, J. Org. Chem., 39, 3793(1974).
Hummel et al., Science, 181, 873 (1973).

*Primary Examiner*—Nicky Chan
*Attorney, Agent, or Firm*—Howard M. Peters; Alan M. Krubiner; Joseph I. Hirsch

[57] ABSTRACT

This process relates to the synthesis of unsaturated aliphatic esters useful as insect sex attractants, including gossyplure, the insect sex pheromone of the pink bollworm moth, *Pectinophora gossypiella*, and intermediates therefor. The process utilizes a cyclic phosphonium (Wittig) reagent.

14 Claims, No Drawings

PREPARATION OF UNSATURATED ALIPHATIC INSECT PHEROMONES USING CYCLIC PHOSPHONIUM YLIDS

FIELD OF THE INVENTION

This invention relates to the synthesis of unsaturated insect pheromones, including (7Z,11Z)- and (7Z,11E)-7,11-hexadecadien-1-yl acetate, gossyplure, of the female pink bollworm moth *Pictinophora gossypiella*, and the intermediates therefor.

BACKGROUND OF THE INVENTION

A frequently used synthetic method for the preparation of unsaturated aliphatic compounds has been the Wittig coupling of an arylphosphonium ylid with an aldehyde or ketone. Suitable procedures for the preparation of ylids and the Wittig reaction are described in A. W. Johnson, "Ylid Chemistry" Academic Press, Inc., New York (1966). The method has proven to be of particular importance in the preparation of unsaturated aliphatic compounds useful as insect sex pheromones. A review describing the preparation of these attractants is "The Synthesis of Insect Sex Pheromones" by Clive A. Hendrick in *Tetrahedron*, Volume 33, pp. 1845–1889 (1977). Additional reports on the preparation of unsaturated alkyl compounds using phosphonium ylids can be found in U.S. Pat. Nos. 3,712,880; 3,732,282; and 3,671,558.

More specifically, the sex pheromone of the female pink bollworm moth has been identified as a mixture of the 7Z,11Z)- and (7Z,11E)-7,11-hexadecadien-1-yl acetate, Hummel, et al., *Science*, 181, 873 (Aug. 31, 1973). A number of syntheses of this pheromone and related compounds have also been described by Anderson and Hendrick in U.S. Pat. Nos. 3,919,329; 3,953,532; 3,987,073; and 3,989,729, and by Sonnet, in the *Journal of Organic Chemistry*, 30, pp. 3793–3794 (1974).

A disadvantage of these described procedures is that the phosphonium ylid used for the coupling normally is used to introduce only one double bond thus necessitating a number of additional chemical reactions, reagents, solvents and so forth to introduce additional double bonds into the aliphatic carbon chain. It has been further found that previously described methods suffer from a number of inherent disadvantages, including multiple reaction steps which lead to poor results for large-scale preparations.

It would therefore be extremely valuable to have a process for preparing unsaturated aliphatic compounds utilizing a single cyclic phosphonium ylid by reaction with a suitable carbonyl derivatives to afford the desired unsaturated aliphatic compounds easily and in high yield and purity, and that is also readily adaptable to large-scale commercial production.

DETAILED DESCRIPTION OF THE INVENTION

The present invention concerns a coupling process whereby a cyclic phosphonium ylid is coupled with a suitably protected aldehyde or ketone to produce the corresponding phosphine oxide in high yield. This compound is subsequently treated with a second aldehyde followed by conversion to an ester, for example, an acetate. Such acetates are valuable and useful as insect sex pheromones in the control of specific insect populations.

These compounds having multiple double bonds have a number of geometrical isomers with different physical and chemical properties. These isomers are described as "trans" designated by "E" and "cis" designated by "Z". Thus, a compound having two carbon-carbon double bonds could have the following isomers: Z,Z; Z,E; E,Z; and E,E. A number usually precedes the letter, e.g., 7Z, to indicate the position of the double bond in the carbon chain.

More specifically, this invention concerns the preparation of specific unsaturated aliphatic compounds and mixtures of compounds, such as (7Z,11)- and (7Z,11Z)-7,11-hexadecadien-1-yl acetate, gossyplure, the insect sex attractant of the pink bollworm moth which is described in U.S. Pat. No. 3,919,329, which is incorporated herein by reference.

The synthesis of this invention is outlined as follows:

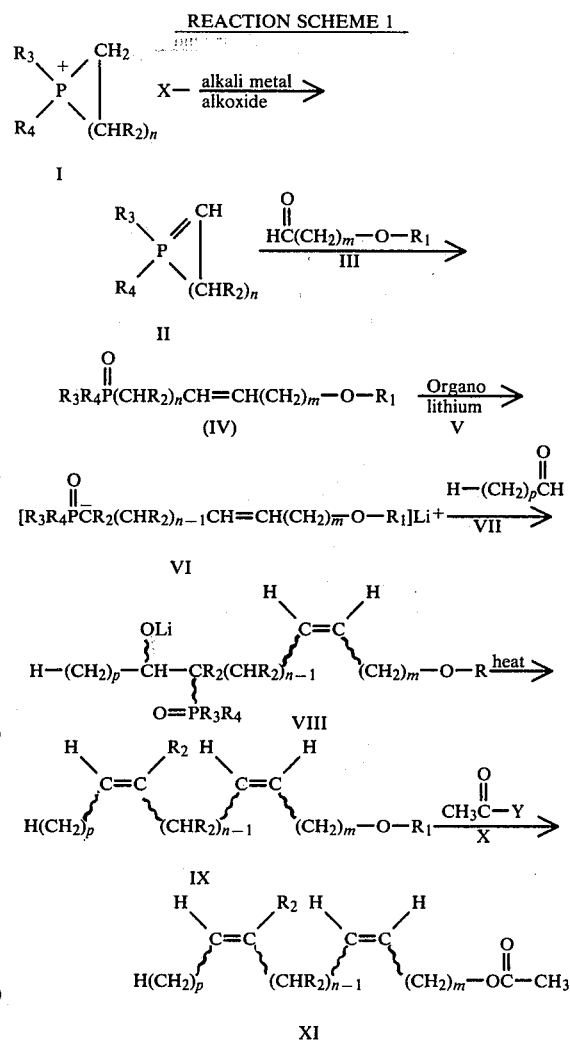

The isomer ratio of Z,E to Z,Z (and E,Z and E,E) for Compounds, such as IX and XI, produced by this process may be changed by changing the order of the addition in the process. Therefore, the process may also be described according to the following sequence:

Reaction Sequence II

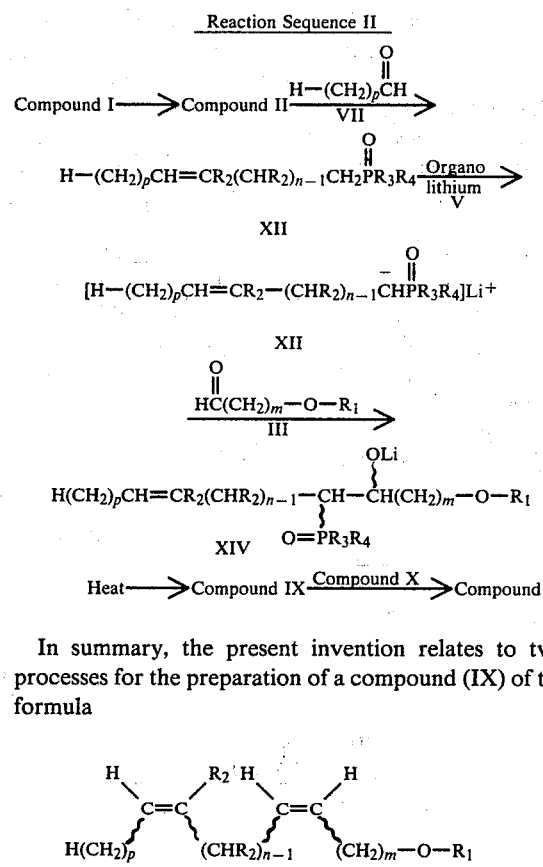

In summary, the present invention relates to two processes for the preparation of a compound (IX) of the formula

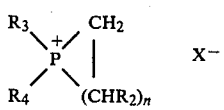

wherein
m is an integer from 1 to 11
n is an integer from 1 to 9
p is an integer from 1 to 6, and
$R_1$ is selected from the group consisting of tetrahydropyranyl, benzyl, triphenylmethyl, trimethylsilyl, t-butyldimethylsilyl;
which first process comprises:
(a) contacting a cyclic phosphonium halide of the formula (I)

(I)

wherein
$R_2$ is selected from the group consisting of hydrogen, and straight and branched chain lower alkyl groups,
$R_3$ and $R_4$ are independently selected from the group consisting of phenyl, lower alkyl-substituted phenyl, lower alkoxy-substituted phenyl, and halo substituted phenyl;
X is a halogen selected from the group consisting of chlorine, bromine, and iodine; and
n is as set forth above,
with an alkali metal alkoxide to produce an ylid of the formula (II)

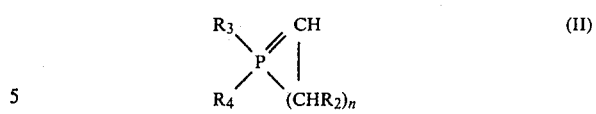

wherein $R_2$, $R_3$, $R_4$ and n are as set forth above;
(b) treating said ylid with a protected hydroxyalkyl aldehyde of formula (III)

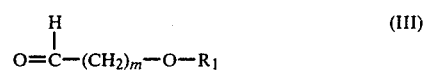

wherein $R_1$ and m are as set forth above, to produce a phosphine oxide of formula (IV)

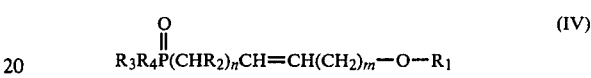

wherein m, n, $R_1$, $R_2$, $R_3$ and $R_4$ are as set forth above,
(c) contacting said compound with an organic lithium compound (V) in an aprotic solvent medium to produce a lithium salt of formula (VI)

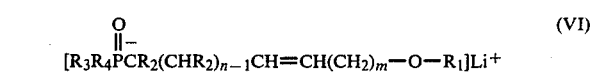

wherein m, n, $R_1$, $R_2$, $R_3$ and $R_4$ are as set forth above,
(d) treating said lithium salt with an aldehyde of formula (VII)

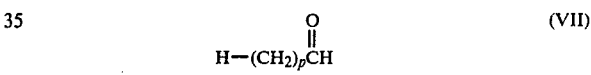

wherein p is an integer from 1 to 6, to produce an alcoholate of formula (VIII)

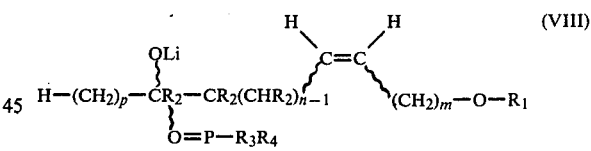

wherein m, n, p, $R_1$, $R_2$, $R_3$ and $R_4$ are as set forth above
(e) heating said alcoholate in an aprotic solvent medium to produce a diene of formula (IX)

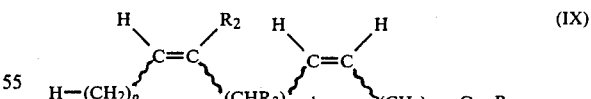

wherein m, n, p, $R_1$, and $R_2$ are set forth above, and which second process comprises:
(a) contacting a cyclic phosphonium halide of formula (I)
wherein n, X, $R_2$, $R_3$ and $R_4$ are as set forth above, with an alkali metal oxide to produce an ylid of the formula (II)
wherein $R_2$, $R_3$, $R_4$ and n are as set forth above,
(b) treating said ylid with an aldehyde of formula (VII) wherein p is an integer from 1 to 6, to produce a phosphine oxide of formula (XII)

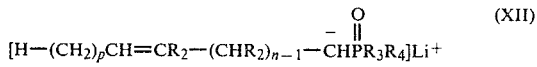

wherein n, p, $R_2$, $R_3$, and $R_4$ are as set forth above, (d) treating said lithium salt with a protected aldehyde of formula III

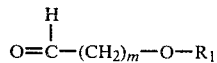

wherein m and $R_1$ are as set forth above, to produce an alcoholate of formula (XIV)

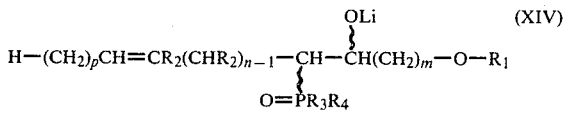

wherein m, n, p, $R_1$, $R_2$, $R_3$ and $R_4$ are set forth above, and (e) heating said alcoholate in an aprotic solvent medium to produce a diene of formula (IX) wherein m, n, p, $R_1$ and $R_2$ are as set forth above.

In both of the above processes there was further included the step of converting the diene of formula (IX) to its corresponding acetate (XI).

The reaction scheme of the invention is shown above in six steps. However, this representation was made only for purposes of clarity of description, and each compound depicted need not be isolated at the end of each such step or purified. Those skilled in the art will recognize that this is, in effect, a three-step process wherein Step 1 progresses from the starting phosphonium halide (I) to the aliphatic phosphine oxide (IV), Step 2 is the conversion of (IV) to the diene (IX); and Step 3 is the optional conversion of (IX) to the acetate derivative (XI).

Phosphonium halides, as represented by Compound (I), are prepared by treating the corresponding hydroxyalkyl diarylphosphine in an aprotic solvent medium with the appropriate hydrogen halide followed by treatment of the product thus formed with a base.

The presently preferred compounds of Formula I are those where n equals 2, 3, 4 or 9. The most preferred compound is when n equals 3. $R_2$ may be selected from the group consisting of hydrogen, and straight and branched chain lower alkyl groups. The lower alkyl groups include those groups containing 1 to 5 carbon atoms, such as the methyl, ethyl, n-propyl, iso-propyl, n-butyl iso-butyl and pentyl groups. The presently preferred compound is where $R_2$ is hydrogen.

$R_3$ and $R_4$ are independently selected from the group consisting of phenyl and phenyl substituted with alkyl groups, alkoxy groups and halogens. Lower alkyl groups include those defined above. Lower alkoxy groups include those straight and branched groups containing 1 to 4 carbon atoms including methoxy, ethoxy, n-propoxy, iso-propoxy and butoxy; and halosubstituted phenyl includes those phenyl compounds substituted at any position with one or more fluorine, chlorine, bromine, or iodine, and combinations thereof. Presently preferred $R_3$ and $R_4$ groups are unsubstituted phenyl.

The solvents used to prepare Compound (I) may be any aprotic solvent capable of forming azeotropic mixtures with water. Presently preferred solvents include benzene, toluene, xylene, n-hexane, n-pentane, ethers, cyclohexane, cyclopentane, and mixtures thereof. A presently preferred solvent is toluene.

The hydrogen halide used to prepare Compound I may include hydrogen chloride, hydrogen bromide and hydrogen iodide. The presently preferred hydrogen halide is hydrogen bromide. The hydrogen halide may also be formed in situ by ordinary methods used in the art.

The usual reaction temperatures employed are in the range between −20° C. and 150° C. Usually the removal of the water during this reaction occurs by azeotropic distillation and the temperature of reaction and water removal will be dictated by the choice of the azeotropic mixture. For example, in a presently preferred mode the azeotropic mixture of toluene and water will boil under standard conditions at about 84° C. The boiling temperature of a normal toluene reaction at reflux will be about 110° C. The time for the reaction to go to completion ranges from several hours to several days, and will depend upon the specific cycloalkyl phosphonium halide being prepared.

Other methods may be used to prepare Compound I that are known to those skilled in this art. For instance, G. A. Gray et al. describes a number of methods in the *Journal of the American Chemical Society*, vol. 98, pp. 2109–2118 (1976) and references cited therein which are incorporated herein by reference.

In the conversion of Compound I to Compound IV or to Compound XII, I is initially treated with an alkyl alkali metal oxide, such as potassium t-butoxide, sodium t-butoxide, calcium t-butoxide, sodium ethoxide, potassium ethoxide, or mixtures thereof. A presently preferred reagent is potassium t-butoxide.

The solvent system for this step should be essentially anhydrous, and an inert gas, such as nitrogen, may be used to maintain anhydrous conditions during the reaction. Further, the solvent may be any aprotic solvent medium, such as ethers, including diethyl ether, tetrahydrofuran, diphenyl ether, diethylene glycol dimethylether, or aromatic and hydrocarbon solvents such as benzene, toluene, xylene, pentane, hexane, cyclohexane, cyclopentane, petroleum ether or mixtures thereof. A presently preferred solvent is tetrahydrofuran.

In Compound III, $R_1$ as a protecting group may be selected from the group consisting of tetrahydropyranyl, benzyl, triphenylmethyl, trimethylsilyl, t-butyldimethylsilyl and the like. A presently preferred group is tetrahydropyranyl. Presently preferred compounds of III are those where m equals 2, 3, 5, 6 or 8. The most preferred is where m equals 6.

The reaction may be conducted at a temperature between −20° C. and 100° C. A presently preferred temperature is about +20° C. The reaction time is in the range of several minutes to 24 hours. A presently preferred method is to form the ylid over about 90 minutes followed by addition of the protected aldehyde (III) and stirring of the reaction mixture for 20–24 hours.

In the conversion of Compound IV (or of Compound XII) to Compound IX, Compound IV is initially treated with an organic lithium Compound V to form the lithium salt VI. The organic lithium compound may be aliphatic or aromatic, such as methyllithium, ethyllithium, propyllithium, butyllithium, pentyllithium, phenyllithium, and benzyllithium. A presently preferred Compound V is n-butyllithium. The solvent for this reaction should be an essentially anhydrous aprotic solvent, such as hexane, pentane, cyclohexane, cycopentane, petroleum ether, benzene, toluene, diethyl ether, tetrahydrofuran and mixtures thereof. A presently preferred solvent mixture is tetrahydrofuran, diethyl ether and hexane. The solvent mixtures may range from 0.1 to 99.9 percent for each component. A presently preferred ratio for tetrahydrofuran, diethyl ether and hexane is about 49/49/2 by volume.

The reaction is initially performed at about −78° C. and is gradually allowed to warm to ambient temperature of about 20° C. as it proceeds.

Presently preferred aldehydes of Formula VII are those where p equals 1, 4 or 5. The most preferred aldehyde VII is where p equals 4.

The lithium salt VIII (or XIV) may be decomposed to the diene IX by various methods. One method is to slowly heat VIII (or XIV) in an aprotic solvent such as hexamethylphophoramide, dimethylformamide, or mixtures thereof at temperatures between 40° and 100° C. A preferred method is to heat VIII in hexamethylphosphoramide at about 70° C. for about two hours. A second preferred method is to treat the salt VIII with water, dissolve in an aprotic solvent and treat with an alkali or alkaline earth hydride, such as sodium hydride, for a few minutes to a few hours. A preferred method is to treat the lithium salt with water, dissolve the alcohol in dimethylformamide and treat with sodium hydride under routine conditions. The reaction mixture is then purified by standard techniques to give the protected diene.

Diene IX is converted to acetate XI by treatment with Compound (X),

wherein Y is selected from the group consisting of chloride, bromide, hydroxy, methoxy, ethoxy, acetoxy and mixtures thereof. A presently preferred method is to dissolve IX in glacial acetic acid (e.g., where Y=hydroxy) followed by acetyl chloride (e.g., where Y=chloride) at about 20° C. for about 30 minutes followed by normal isolation and purification.

Specifically, the process with minor variations is useful to prepare the following insect sex pheromones; (9Z,12E)-9,12-tetradecadienyl-1-acetate, of the almond moth (*Cadra cautella*) and also the Indian meal moth (*Plodia interpunctella*); (4E,7Z)-4,7-tridecadienyl-1-yl acetate of the potato tuberworm moth (*Phthorimaea operculella*); (7Z,11E)-and (7Z,11Z)-7,11-hexadecadien-1-yl acetate of the pink bollworm moth (*Pectinophora gossypiella*), the 7Z,11E isomer of the angoumois grain moth (*Sitograga cerealella* Oliv), and also the (7E,11Z)- and (7Z,11Z)- isomers of the cherry tree borer moth (*Synanthedon hector*); (3E,13Z) and (3Z,13Z)-3,13-octadecadien-1-yl acetate of the lesser peachtree borer (*Synanthedon pictipes*) and the peachtree borer (*Sanninoidea exitiosa*); and (6E,11Z)-6,11-hexadecadien-1-yl acetate of the polyphemus moth (*Antherea polyphemis*).

In a similar manner, the following insect pheromones may also be prepared: (8E,10E)-8,10-dodecadien-1-ol, of the coddling moth (*Laspeyresia pomonella*); (7E,9Z)-7,9-dodecadien-1-yl acetate, of the European grapevine moth (*Lobesia botrana*); (E)-9,11-dodecadien-1-yl acetate, of the red bollworm moth (*Diparopsis castanea*); (9Z,11E)-9,11-tetradecadien-1-yl acetate, of the Egyptian cotton leafworm (*Spodoptera littoralis*), and (10E,12Z)-10,12-hexadecadien-1-ol, of the silkworm moth (*Bombyx mori*).

The most preferred application of this process is the preparation of the about 1 to 1 mixture of (7Z,11E) and (7Z,11Z)-7,11-hexadecadienyl-1-yl acetate gossyplure as the insect sex pheromone of the pink bollworm moth (*Pectinophora gossypiella*).

The isomerism of the carbon-carbon double bonds (E or Z) in the compounds produced by this process may be fixed as a result of stereospecific or stereoselective syntheses. However, this isomerism (E or Z) may be altered by standard equilibration or isomerization techniques, such as halogenation and dehalogenation, that are well known in the art. Such olefin isomer transformations are described, for instance, by P. E. Sonnet, *Journal of Organic Chemistry*, vol. 45, pp. 154–157, (1980) which is incorporated herein by reference.

The mixture of the isomers formed (E,E; E,Z; Z,E; and Z,E) are separable from the reaction mixture and from each other by virtue of their different physical properties using conventional separation techniques, such as chromatography (including thin layer, gas-liquid, and high pressure liquid chromatography) and also fractional distillation.

The isomer ratio of Z,E to Z,Z (and E,Z and E,E), for the compounds produced by this process may also be altered in the conversion of IV to VI to VIII by using different aprotic solvents, addition temperatures or methods of decomposition. The effect of changing these variables is shown in the following table:

| (7Z,11E)- and (7Z,11Z)-7,11-Hexadecadiene-1-yl Acetate (Z,E/Z,Z ratio) (Changes due to solvent, temperature, decomposition method) | | | | |
|---|---|---|---|---|
| | Addition temp. | | Method of | Isomer Radio |
| Solvent | n-buLi[a] | aldehyde[b] | decomposition | % ZE | % ZZ |
| Et$_2$O[c] | −78° C. | 20° C. | NaH[d]/DMF[e] | 61.4 | 38.6 |
| Et$_2$O | −78° C. | −78° C. | NaH/DMF | 68.4 | 31.6 |
| THF[f] | −78° C. | −78° C. | HMPA[g]/heat | 41.7 | 58.3 |
| THF | −78° C. | −78° C. | HMPA/heat | 37.2 | 62.8 |
| hexane/ Et$_2$O(9:1) | −78° C. | −78° C. | HMPA/heat | 55.8 | 44.2 |
| THF/ Et$_2$O(1:1) | −78° C. | −78° C. | HMPA/heat | 54.4 | 45.6 |
| HMPA | 0° C. | 0° C. | HMPA/heat | 33.6 | 66.3 |

[a]n-buLi is n-butyllithium
[b]aldehyde is valeraldehyde
[c]Et$_2$O is diethyl ether
[d]NaH is sodium hydride
[e]DMF is dimethylformamide
[f]THF is tetrahydrofuran
[g]HMPA is hexamethylphosphoramide Another aspect of the invention is the preparation of novel Compounds, including Compounds IV, VI, VIII, IX, XII, XIII and XIV.

DESCRIPTION OF SPECIFIC EMBODIMENT

The following specific description and examples are given to enable those skilled in this art to understand and practice the present invention. It should not be considered as a limitation upon the scope of the invention but merely as being illustrative and representative thereof. All temperatures are reported in degrees Centigrade.

EXAMPLE 1

A solution of 103 g of 4-hydroxybutyldiphenylphosphine in 150 ml of toluene is added at room temperature to 1.5 liters of toluene saturated with hydrogen bromide with stirring. The resulting milky suspension is brought to reflux with azeotropic removal of water using a Dean-Stark trap. After one hour the mixture is cooled to 80° and resaturated with hydrogen bromide. The suspension is then brought to reflux and maintained for one hour, after which the mixture was again saturated with hydrogen bromide. The reaction mixture is then maintained at reflux overnight, and allowed to cool to room temperature. The supernatant toluene was decanted from the residual oil, and was replaced with 1.5 liters (1) of water containing 80 g. each of sodium carbonate and sodium bicarbonate. The resulting aqueous mixture is stirred for 72 hours at room temperature, saturated with sodium bromide and extracted six times with 300 ml of chloroform. The combined organic layers are dried over sodium sulfate, filtered and evaporated to yield 94.1 g, a 71% yield based on theoretical, of tetramethylene 1,1-diphenylphosphonium bromide, which on trituration with acetone has a melting point of 163°–4°.

Repeating the above procedure, in a similar manner, and substituting a stoichiometrically equivalent of
2-hydroxyethyldiphenylphosphine,
3-hydroxypropyldiphenylphosphine,
5-hydroxypentyldiphenylphosphine,
6-hydroxyhexyldiphenylphosphine,
7-hydroxyheptyldiphenylphosphine,
8-hydroxyoctyldiphenylphosphine,
9-hydroxynonyldiphenylphosphine, and
10-hydroxydecyldiphenylphosphine for
4-hydroxybutyldiphenylphosphine there are obtained the following cyclic phosphonium compounds:
dimethylene-1,1-diphenylphosphonium bromide
trimethylene-1,1-diphenylphosphonium bromide,
pentamethylene-1,1-diphenylphosphonium bromide,
hexamethylene-1,1-diphenylphosphonium bromide,
heptamethylene-1,1-diphenylphosphonium bromide,
octamethylene-1,1-diphenylphosphonium bromide,
nonamethylene-1,1-diphenylphosphonium bromide, and
decamethylene-1,1-diphenylphosphonium bromide.

EXAMPLE 2

To 24.1 g of solid tetramethylene 1,1-diphenylphosphonium bromide and 8.42 g of potassium t-butoxide under a blanket of nitrogen is added 100 ml of anhydrous tetrahydrofuran using a syringe. The resulting orange solution is allowed to stir one hour at room temperature. Using a syringe, 10.7 g of 7-(2-tetrahydropyranyloxy)heptanal was added over 30 minutes, which resulted in a noticeable rise in temperature. The reaction is allowed to stir overnight at room temperature, then was quenched with 50 ml of water. The mixture is partitioned between 200 ml of diethyl ether and water, and the resulting organic layer is washed three times with 100 ml of water and three times with 100 ml of brine. The organic extract is dried, filtered through silica gel, and evaporated to yield 22.3 g of 11-(2-tetrahydropyranyloxy)-4Z-undecenyldiphenylphosphine oxide.

Repeating the above procedure in a similar manner, and substituting a stoichiometrically equivalent of
2-(2-tetrahydropropanyloxy)acetaldehyde,
3-(2-tetrahydropyranyloxy)propanal,
4-(2-tetrahydropyranyloxy)butanal,
5-(2-tetrahydropyranyloxy)pentanal,
6-(2-tetrahydropyranyloxy)hexanal,
8-(2-tetrahydropyranyloxy)octanal, and
9-(2-tetrahydropyranyloxy)nonanal for
7-(2-tetrahydropyranyloxy)heptanal, there are obtained the following diaryl alkyl phosphine oxides:
6-(2-tetrahydropyranyloxy)-4Z-hexenyldiphenylphosphine oxide,
7-(2-tetrahydropyranyloxy)-4Z-heptenyldiphenylphosphine oxide,
8-(2-tetrahydropyranyloxy)-4Z-octenyldiphenylphosphine oxide,
9-(2-tetrahydropyranyloxy)-4Z-nonenyldiphenylphosphine oxide,
10-(2-tetrahydropyranyloxy)-4Z-decenyldiphenylphosphine oxide,
12-(2-tetrahydropyranyloxy)-4Z-dodecenyldiphenylphosphine oxide, and
13-(2-tetrahydropyranyloxy)-4Z-tridecenyldiphenylphosphine oxide.

EXAMPLE 3

To a cooled solution of 0.45 g of 11-(2-tetrahydropyranyloxy)-4Z-undecenyldiphenylphosphine oxide in 10 ml of dry tetrahydrofuran/diethyl ether (50/50) is added 0.75 ml of 1.6 M n-butyllithium in hexane, 1.2 mmol) dropwise using a syringe. After 15 min, 0.132 ml of n-valeraldehyde is added using a syringe, and the resulting solution is stirred 30 minutes, then allowed to warm to room temperature. The lithium salt is obtained, and can then be decomposed by either of the following two methods, both monitored by thin layer chromatography:

A. via heating in HMPA—Addition of 5 ml of hexamethylphosphoramide to the lithium salt followed by warming for 2 hours at 70° affected decomposition to a mixture of the dienes, (7Z,11E)- and (7Z,11Z)-7,11-hexadecadien-1-yl 1-tetrahydropyranate.

B. via NaH in DMF—Decomposition of the lithium salt to the alcohol by aqueous extraction, followed by dissolution in 5 ml of dimethylformamide, and addition of 0.12 g of sodium hydride affected decomposition to the dienepyranates in approximately 30 minutes.

In both cases, the reaction mixture is partitioned between ether and water, and the organic layer is washed with brine, dried over sodium sulfate, filtered and evaporated to give the crude tetrahydropyranates.

The crude diene-tetrahydropyranates are dissolved in glacial acetic acid (2 ml) and to the solution is added 1 ml of acetyl chloride. The reaction mixture is stirred at room temperature for 30 minutes, at which time thin layer chromatography shows complete conversion to diene acetates.

The mixture is partitioned between ether and water, and the acetic acid carefully quenched by cautious portionwise addition of solid sodium bicarbonate. The organic layer is washed with saturated aqueous bicarbonate and brine, dried with sodium sulfate, filtered and evaporated to give an amber oil, and purified by column chromatography on silica gel in methylene chloride to yield 180 mg of (7Z,11E)- and (7Z,11Z)-7,11-hexadecadien-1-yl acetate mixture, as a clear colorless oil. The nearly 1:1 ratio of isomers is determined by gas-liquid chromatography.

On a larger scale, the diene acetates are purified by distillation.

Repeating the above procedure in a similar manner, and substituting a stoichiometrically equivalent of
acetaldehyde,
n-propanol,
n-butanal,
n-hexanal,
n-heptanal,
n-octanal, and
n-nonanal for n-valeraldehyde,
there are obtained the following mixtures of diene acetates:
7,11-tridecadien-1-yl acetate,
7,11-tetradecadien-1-yl acetate,
7,11-pentadecadien-1-yl acetate,
7,11-heptadecadien-1-yl acetate,
7,11-octadecadien-1-yl acetate,
7,11-nonadecadien-1-yl acetate, and
7,11-eicosadien-1-yl acetate.

By substituting a stoichiometrically equivalent of 3-hydroxypropyldiphenylphosphine oxide for 4-hydroxybutyldiphenylphosphine oxide in Example 1, 9-(2-tetrahydropyranyloxy)nonanal for 7-(2-tetrahydropyranyloxy)heptanal in Example 2, and acetaldehyde for n-valeraldehyde in Example 3, respectively there is obtained (9Z,12Z)- and (9Z,12E)-9,12-tetradecadien-1-yl acetate. A presently preferred process is where m is 8, n is 2, p is 1, $R_1$ is tetrahydropyranyl, $R_2$ is hydrogen, and $R_3$ and $R_4$ are phenyl.

By substituting a stoichiometrically equivalent of 3-hydroxypropyldiphenylphosphine oxide for 4-hydroxybutyldiphenylphosphine oxide in Example 1, 4-(2-tetrahydropyranyloxy)butanal for 7-(2-tetrahydropyranyloxy)heptanal in Example 2, and n-hexanal for n-valeraldehyde in Example 3, there is obtained (4Z,7Z)- and (4Z,7E)-tridecadien-1-yl acetate. A presently preferred process is where m is 3, n is 2, p is 5, $R_1$ is tetrahydropyranyl, $R_2$ is hydrogen, and $R_3$ and $R_4$ are phenyl.

By substituting 10-hydroxydecyldiphenylphosphine for 4-hydroxybutyldiphenylphosphine oxide in Example 1, 3-(2-tetrahydropyranyloxy)propanal for 7-(2-tetrahydropyranyloxy)heptanal in Example 2, and using n-valeraldehyde as in Example 3, there is obtained (3Z,13Z)- and (3E,13Z)-3,13-octadecadien-1-yl acetate. A presently preferred process is where m is 2, n is 9, p is 4, $R_1$ is tetrahydropyranyl, $R_2$ is hydrogen, and $R_3$ and $R_4$ are phenyl.

By substituting 5-hydroxypentyldiphenylphosphine for 4-hydroxybutyldiphenylphosphine oxide as in Example 1, 6-(2-tetrahydropyranyloxy)hexanal for 7-(2-tetrahydropyranyloxy)heptanal in Example 2, and using n-valeraldehyde as in Example 3, there is obtained (6Z,11Z)- and (6Z,11E)-6,11-hexadecadien-1-yl acetate. A presently preferred process is where m is 5, n is 4, p is 4, $R_1$ is tetrahydropyranal, $R_2$ is hydrogen, and $R_3$ and $R_4$ are phenyl.

The products of Example 2 or the final products of Example 3 are equilibrated by standard techniques to produce a mixture of stereochemical isomers which are then separated by chromatography (including thin layer or gas-liquid high pressure liquid chromatography) and or fractional distillation.

The present invention has been described with reference to the specific embodiments thereof, it should, however, be noted and understood by those skilled in this art that various changes may be made and equivalents may be substituted without departing from the spirit and scope of the invention. Further, many modifications may be made to adapt a particular situation, material, or composition of matter, process, process step or steps, or then-present objective to the spirit of this invention without departing from its essential teachings.

What is claimed is:

1. A process for the preparation of a compound of the formula:

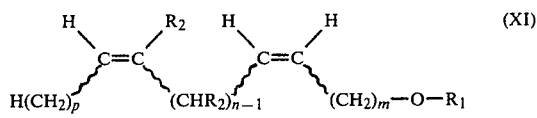

wherein
m is an integer from 1 to 11,
n is an integer from 1 to 9,
p is an integer from 1 to 6,
$R_1$ is selected from the group consisting of tetrahydropyranyl, benzyl, trimethylsilyl, t-butyldimethylsilyl and triphenylmethyl;
which process comprises:
(a) contacting a cyclic phosphonium halide of the formula:

wherein
n is as set forth above,
$R_2$ is selected from the group consisting of hydrogen, and straight and branched chain lower alkyl groups,
$R_3$ and $R_4$ are independently selected from the group consisting of phenyl, lower alkyl-substituted phenyl, lower alkoxy-substituted phenyl, and halo substituted phenyl; and
X is a halogen selected from the group consisting of chlorine, bromine, and iodine;
with an alkali metal alkoxide to produce a ylid of the formula:

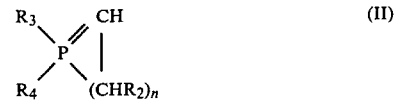

wherein n, $R_2$, $R_3$ and $R_4$ are as set forth above;
(b) treating said ylid with a protected hydroxy alkyl aldehyde of the formula

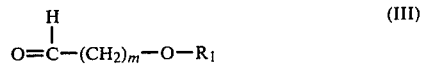

wherein $R_1$ and m are as set forth above, to produce a phosphine oxide of the formula:

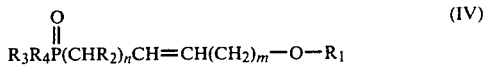

wherein m, n, $R_1$, $R_2$, $R_3$ and $R_4$ are as set forth above;

(c) contacting said phosphine oxide with an organo lithium compound in an aprotic solvent medium to produce a lithium salt of the formula:

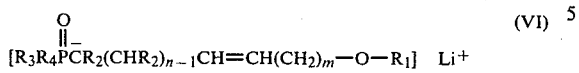

wherein m, n, $R_1$, $R_2$, $R_3$, and $R_4$ are as set forth above;

(d) treating said lithium salt with an aldehyde of the formula:

wherein p is as set forth above to produce an alcoholate of the formula:

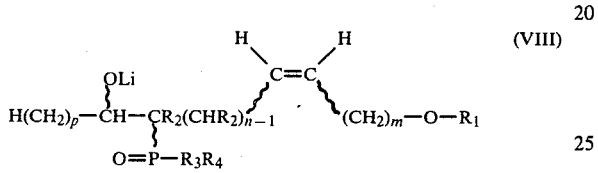

wherein m, n, p, $R_1$, $R_2$, $R_3$ and $R_4$ are as set forth above; and (e) heating said alcoholate in an aprotic solvent medium to produce a diene of the formula:

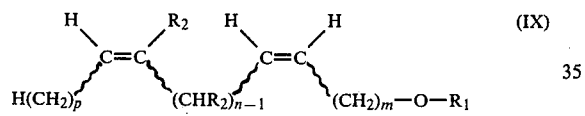

wherein m, n, p, $R_1$, and $R_2$ are as set forth above.

2. A process for the preparation of a compound of the formula:

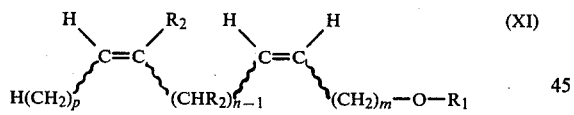

wherein
m is an integer from 1 to 11,
n is an integer from 1 to 9,
p is an integer from 1 to 6,
$R_1$ is selected from the group consisting of tetrahydropyranyl, benzyl, trimethylsilyl, t-butyldimethylsilyl and triphenylmethyl;
which process comprises:

(a) contacting a cyclic phosphonium halide of the formula:

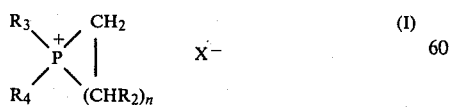

wherein
n is as set forth above,
$R_2$ is selected from the group consisting of hydrogen, and straight and branched chain lower alkyl groups, $R_3$ and $R_4$ are independently selected from the group consisting of phenyl, lower alkyl-substituted phenyl, lower alkoxy-substituted phenyl, and halo substituted phenyl; and X is a halogen selected from the group consisting of chlorine, bromine, and iodine;

with an alkali metal alkoxide to produce an ylid of the formula:

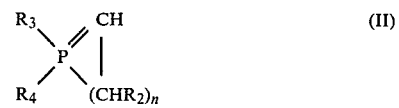

wherein n, $R_2$, $R_3$ and $R_4$ are as set forth above;

(b) treating said ylid with an aldehyde of the formula

wherein p is as set forth above, to produce a phosphine oxide of the formula:

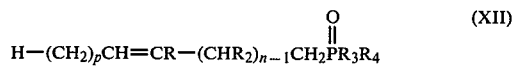

wherein n, p, $R_2$, $R_3$ and $R_4$ are as set forth above;

(c) contacting said phosphine oxide with an organo lithium compound in an aprotic solvent medium to produce a lithium salt of the formula:

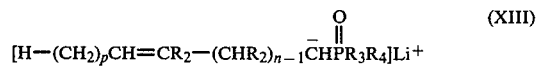

wherein n, p, $R_2$, $R_3$, and $R_4$ are as set forth above;

(d) treating said lithium salt with a protected hydroxy aldehyde of the formula:

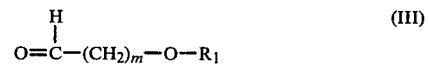

wherein m and $R_1$ are set forth above to produce an alcoholate of the formula:

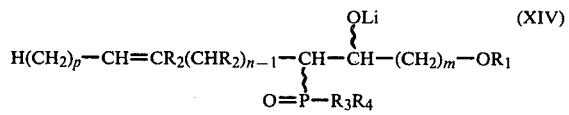

wherein m, n, p, $R_1$, $R_2$, $R_3$ and $R_4$ are as set forth above; and (e) heating said alcoholate in an aprotic solvent medium to produce a diene of the formula:

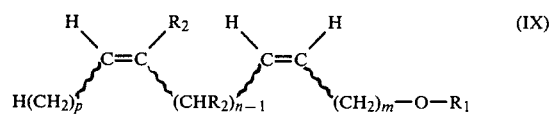

wherein m, n, p, $R_1$, and $R_2$ are as set forth above.

3. The process of claim 1 or 2 further including the step of converting said diene to its corresponding acetate.

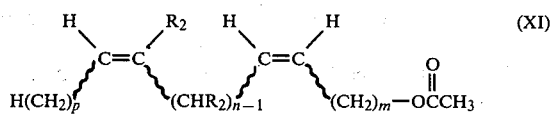

4. The process of claim 3 wherein said diene is converted to said acetate by treatment of said diene with a compound of the formula:

wherein Y is selected from the group consisting of chloride, bromide, methoxy, ethoxy, acetoxy, and mixtures thereof.

5. The process of claim 1 or 2 wherein steps (c) and (d) are performed at a temperature between $+20°$ and $-78°$ C.

6. The process of claim 5 wherein said aprotic solvent medium in steps (c) or (e) is selected from the group consisting of diethylether, tetrahydrofuran, hexane, hexamethylphosphoramide, dimethylformamide and mixtures thereof.

7. The process according to claim 1 or 2 wherein Compound IX is produced by replacement of Step (e) by treatment with a water solution in a dipolar aprotic solvent medium and treatment with an alkali or alkaline earth metal hydride.

8. The process of claim 3 wherein a mixture of (7Z,11Z) and (7Z,11E)-7,11-hexadecadien-1-yl acetates is prepared.

9. The process of claim 8 wherein a mixture of (7Z,11Z) and (7Z,11E)-7,11-hexadecadien-1-yl acetates is produced in a ratio of about 1 to 1.

10. The process of claim 3 wherein (9Z,12E)-9,12-tetradecadiene-1-yl acetate is prepared.

11. The process of claim 3 wherein (4E,7Z)-4,7-tridecadien-1-yl acetate is prepared.

12. The process of claim 3 wherein a mixture of (3E,13Z)- and (3Z,13Z)-3,13-octadecadien-1-yl acetates is prepared.

13. The process of claim 12 wherein a mixture of (3E,13Z)- and (3Z,13Z)-3,13-octadecadien-1-yl acetates is prepared in a ratio of about 1 to 1.

14. The process of claim 3 wherein (6E,11Z)-6,11-hexadecadien-1-yl acetate is prepared.

* * * * *